United States Patent [19]

Gassman et al.

[11] Patent Number: 4,582,578
[45] Date of Patent: Apr. 15, 1986

[54] METHOD FOR THE ELECTROCHEMICAL CONVERSION OF A QUADRICYCLANE TO A NORBORNADIENE

[75] Inventors: Paul G. Gassman, St. Paul, Minn.; James W. Hershberger, Oxford, Ohio

[73] Assignee: Regents of the University of Minnesota, Minneapolis, Minn.

[21] Appl. No.: 762,111

[22] Filed: Aug. 2, 1985

[51] Int. Cl.⁴ .......................... B01J 19/12; C25B 3/00
[52] U.S. Cl. .................................. 204/59 R; 204/231; 204/158.14
[58] Field of Search .................. 204/59 R, 162 R, 231

[56] References Cited

U.S. PATENT DOCUMENTS 2,835,631  5/1958  Metcalf et al. ...................... 204/231
4,446,041  5/1984  Neory .............................. 204/158 R

OTHER PUBLICATIONS

K. Maruyama et al., Chem. Letters, 839 (1981).
K. Maruyama et al., Chem. Letters, 1259 (1980).
R. W. Hoffmann et al., J. Chem. Soc. Chem. Commun. 345 (1983).
H.-D. Scharf et al., Angew. Chem. Int. Ed. Engl., 18, 652 (1979).
K. Maruyama et al., J. Org. Chem., 46, 5294 (1981).
C. Phillippopoulos et al., Ind. Eng. Chem. Prod. Res. Dev., 22, 627 (1983).
H. Hirao et al., J. Chem. Soc., Chem. Commun. 300 (1984).
P. Delahay, Instrumental Analysis, the Macmillon Co., (1957), pp. 118-139.

Primary Examiner—Howard S. Williams
Attorney, Agent, or Firm—Merchant, Gould, Smith, Edell, Welter & Schmidt

[57] ABSTRACT

A method based on a cyclic single electron transfer mechanism has been developed for the electrochemical initiation and interruption of the exothermic quadricyclane to norbornadiene conversion.

14 Claims, 1 Drawing Figure

METHOD FOR THE ELECTROCHEMICAL CONVERSION OF A QUADRICYCLANE TO A NORBORNADIENE

The invention was made with Government support under contract number 8114772-A02 awarded by the National Science Foundation. The Government has certain rights in this invention.

BACKGROUND OF THE INVENTION

Most of the solar energy collection systems presently in use act to convert solar radiation into heat or electricity, neither of which can be stored for later use as such. One solution to this problem involves the use of solar radiation to drive photochemical processes which result in the production of stable, high energy fuels. For example, the reactions involved in photosynthesis lead to the storage of solar energy in organic fuels such as wood, which can later be burned to produce heat and light. However, the solar production of biomass is not an ideal energy-storage system for man, except with respect to its use as food, since its cultivation requires large amounts of land, water, fertilizers, and is labor-intensive.

While the efficiency of solar energy storage by the complex reactions involved in photosynthesis is about 6–8%, the thermodynamic limitation for photochemical energy storage is about 15–20%. Therefore, considerable research has been directed to the synthesis of compounds which can form energy-rich products upon absorption of solar radiation. The energy thus stored must be regainable at a later date, with simultaneous recovery of the starting material. In recent years, the photochemical storage of solar energy in highly-strained organic molecules has been widely investigated, both theoretically and experimentally. The energy-storing photochemical reaction A→B should proceed in a high chemical yield; preferably greater than 99%, and exhibit an enthalpy of reaction of greater than about 500 J/g. With or without a sensitizer, chemical A should absorb a large percentage of the photochemically effective solar spectrum range (300–700 nm). Compound B should be stable over long periods of time and be reconvertable back to A in high yield.

The high energy storage capacity required by this process has lead to the investigation of isomerizations of A-type molecules which lead to small rings. The valence isomerization between norbornadiene (NBD) and quadricyclane (Q) is one of the most promising of these systems.

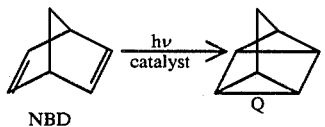

Although the enthalpy of isomerization of norbornadiene to quadricyclane is moderate (110 kJ/mol), the low molecular weight (92) means that an exceptionally high storage capacity of 1200 J/g results. Furthermore, Q is extremely stable, the half-life for conversion back to NBD at 140° C. being at least 14 hours. However, either the utilization of an appropriate sensitizer or the introduction of substituents is required to realize a facile NBD→Q isomerization under sunlight, since norbornadiene itself does not absorb solar radiation of greater wavelengths than 300 nm. For example, K. Maruyama et al., in *Chemistry Letters*, 839 (1981) have reported that 3-phenylcarbamoyl-2,5-norbornadiene-2-carboxylic acid readily undergoes valence isomerization into the corresponding quadricyclane derivative upon exposure to sunlight. Extensive studies on the metal complex-catalyst photoisomerization of norbornadienes to quadricyclanes have also been carried out. See K. Maruyama et al., *Chemistry Letters*, 1259 (1980) K. Maruyama, et al., *Chemistry Letters*, 743 (1984), and H.-D. Scharf et al., *Angew. Chem. Int. Ed. Engl.*, 18, 652 (1979). While most of the problems associated with the photochemical conversion of norbornadienes to quadricyclanes have apparently been solved, attempts to develop a simple method for the controlled release of energy from quadricyclanes have been less successful.

For example, R. W. Hoffmann et al., in *J. Chem. Soc., Chem. Commun.*, 345 (1983) have disclosed that the addition of small amounts of stable tris-(p-bromophenyl)aminium salts to quadricyclane solutions catalyzes the Q→NBD isomerization. These salts presumably generate the cation radical of Q (Q·+) which spontaneously isomerizes to the cation radical of NBD. However, once initiated, the conversion of Q to NBD continues to completion or until the quadricyclane cation radical is deactivated by side reactions. Furthermore, the high cost of the aminium salts, which are consumed during the reaction, also presents a commercial obstacle to the large scale use of this method to release the energy stored in quadricyclanes.

Therefore, a need exists for a method to convert quadricyclanes to the corresponding norbornadienes in high yield. A need also exists for a method of converting quadricyclanes to norbornadienes which can be interrupted and restarted. A further need exists for a method to convert quadricyclanes to norbornadienes which is energetically-favorable with respect to the total energy balance of the system.

BRIEF DESCRIPTION OF THE INVENTION

The present invention provides an efficient, readily-controlled method for electrochemically initiating the conversion of a quadricyclane to the corresponding norbornadiene. The exothermic quadricyclane to norbornadiene conversion can be switched on and off through the use of a carrier oxidant compound such as a triarylamine which can be anodically oxidized to the corresponding cation radical. The cation radical in turn functions to oxidize the quadricyclane to the unstable quadricyclane cation radical. The quadicyclane-norbornadiene conversion which results can be readily halted by the electrical reduction of the cation radical of the carrier oxidant back to the inactive neutral (uncharged) form.

According to one embodiment of the invention, an electroconductive solution is prepared which comprises the quadricyclane and the triarylamine. An anodic potential is applied to the solution effective to oxidize the triaryl amine to the corresponding triarylamine cation radical which in turn oxidizes the quadricyclane to the corresponding quadricyclane cation radical by means of a single electron transfer (SET) from the quadricyclane to the triaryl ammonium cation, thus regenerating the neutral triarylamine. The unstable quadricyclane cation radical readily isomerizes to the norbornadiene cation radical which is itself reduced to norbornadiene. The exothermic Q→NBD reaction releases heat into the solvent which can be recovered by conventional means.

Since the reduction of the norbornadiene cation radical can occur by SET form the quadricyclane or the triarylamine, thus regenerating the active quadricyclane or triarylamine cation radicals, the Q→NBD isomerization is substantially self-perpetuating and only relatively small amounts of externally-applied current are required to maintain the isomerization reaction. In view of the thermal energy released, extremely high energy gains can be realized by the present method.

Furthermore, the Q→NBD isomerization can be stopped immediately by the application of a cathodic potential to the electroconductive solution and restarted through the reapplication of the anodic potential. Thus the conversion of Q→NBD can be turned on and off at will, permitting the controlled release of the solar energy stored in the quadricyclane molecule.

As used herein, the term "electroconductive solution" is intended to refer to a solution containing an electrolyte at a concentration sufficient to permit the passage of the current necessary to accomplish the reactions of this invention at the required potential differentials.

As used herein, the term "a quadricyclane" is intended to refer to both unsubstituted quadricyclane (quadricyclo[2.2.1.0$^{2,6}$.0$^{3,5}$]heptane) and to substituted quadricyclanes which are capable of being converted to the corresponding substituted norbornadiene by the present process. Likewise, the term "a norbornadiene" is intended to refer both to the parent compound, bicyclo[2.2.1]hepta-2,5-diene, as well as to substituted norbornadienes which are useful in the practice of the invention.

DETAILED DESCRIPTION OF THE INVENTION

Figure 1:
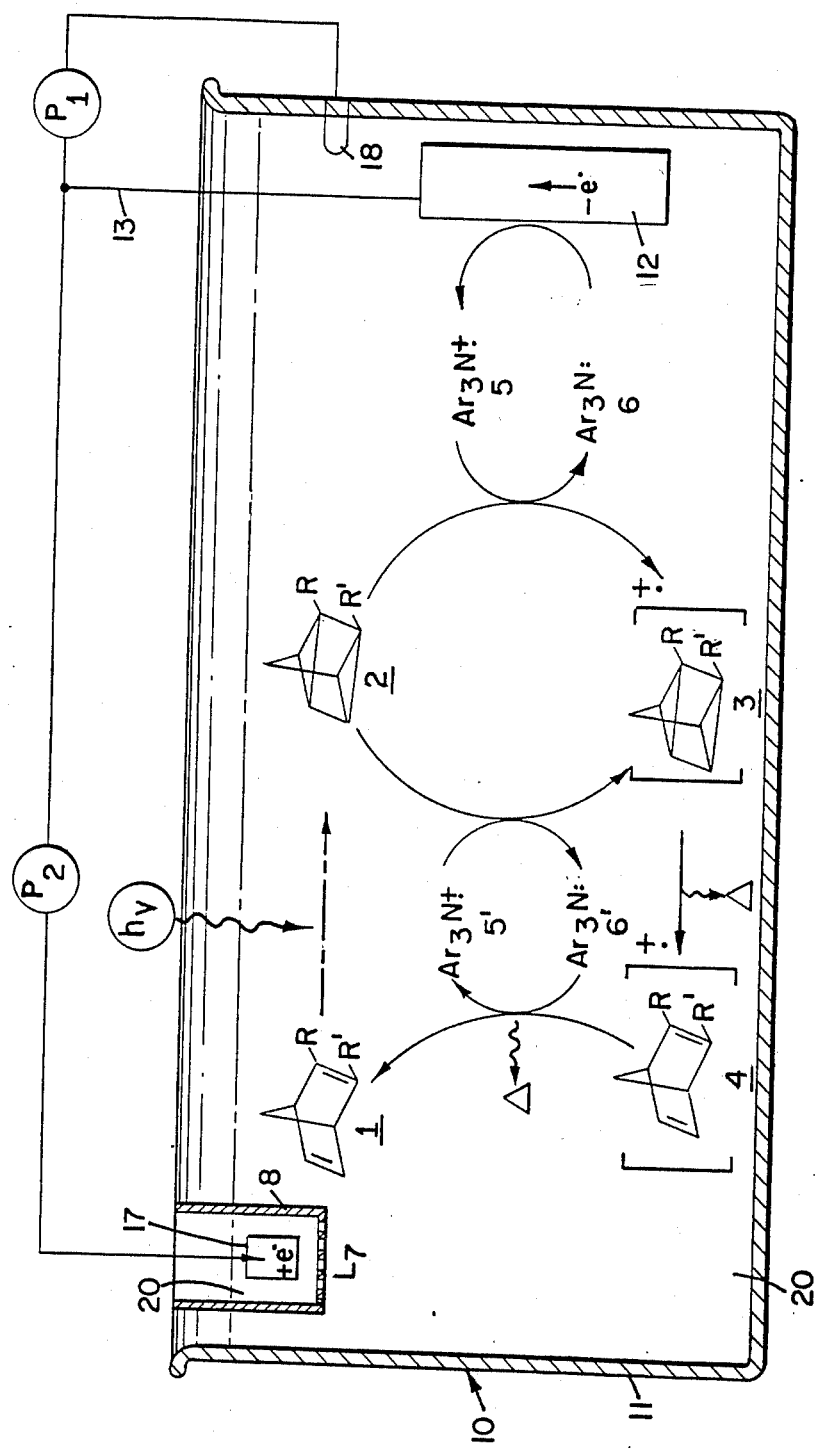

The method of the present invention will be described by reference to the FIGURE, which represents a schematic cross-sectional view of a reaction cell in which a quadricyclane is converted to the corresponding norbornadiene utilizing the method of the present invention.

The cell 10 depicted in the FIGURE is a three-compartment-type electrolysis cell. Such cells are commercially-available and are employed for coulometric titrations at controlled potential, as described by P. Delahay in *Instrumental Analysis*, the Macmillan Co. (1957) at pages 118–139, the disclosure of which is incorporated by reference herein. Cell 10 comprises a primary reservoir 11, containing working electrode 12 in electrical connection via wire 13 with a current source $P_2$ of reversible potential and with counter-electrode 17. The electrodes are formed of chemically-inert substances such as glassy carbon, graphite, platinum and the like. Working electrode 12 is also in electrical connection with reference electrode 18, e.g., a saturated calomel electrode, via potentiostat $P_1$.

Primary reservoir 11 contains solvent 20 which is rendered electroconductive by an effective amount of a dissolved electrolyte. The solvent is preferably selected to have a high heat capacity and must be capable of dissolving the quadricyclane, the norbornadiene, the electrolyte and the amine catalyst to the desired concentration, e.g., from about 0.01–3.0 moles of NBD or Q per liter of solvent. The solvent is also selected so as to be non-reactive with the radical cation species which are formed in the cell, e.g. it should possess no substantial nucleophilicity. Therefore, suitable organic solvents can include cyclohexane, acetonitrile and the halogenated hydrocarbons such as methylene chloride, chloroform, trichloroethylenes, 1,1,1-trichloroethane and the like. Polyhalogenated hydrocarbons containing fluorine and chlorine (The Freon ® series, E. I. DuPont DeNemours and Co.) and the dimethylpolysiloxanes (the Rhodorsil ® series, Rhone-Poulenic Inc.) can also be useful as solvents in the present method. Mixtures of two or more compatible organic solvents can also be employed to maximize the concentration of the reactive species.

The electrolyte can be selected from any of the inorganic or organic salts which can be dissolved in the organic solvent to the extent necessary to carry the current required. Organic salts are preferred as electrolytes due to their higher solubility in nonpolar solvents, and include quaternary (tetraalkyl)ammonium salts, e.g. (tetrahexyl)ammonium perchlorate (tetrabutyl)ammonium perchlorate and the like.

The electroconductive solvent will also incorporate a quadricyclane 2, which as depicted in the FIGURE can be quadricyclane itself (2, R=R'=H) or can be substituted at any or all of carbons 1, 2, 3, 4, 5, 6, 7, or 7'. Although quadricyclane 2 can be produced from the corresponding norbornadiene 1 by direct exposure of the electrolysis cell to solar radiation (hν), it is preferable that a solution of norbornadiene 1 and the triaryl amine 6 in the electroconductive solvent 20 be isomerized in a separate energy collector unit (not shown). Once the desired concentration of quadricyclane 2 has been generated, the quadricyclane-amine containing solution is flowed into the cell 10 and the heat-releasing isomerization reaction electrically initiated, according to the present invention. The heat generated by the Q→Q$^+$·→NBD$^+$·→NBD reaction raises the temperature of solvent 20. This heat can be captured and/or transmitted to the end-use site by conventional means, such as heat exchangers (not shown). The NBD-rich solution can then be returned to the collector unit and the system recharged. Systems for the solar isomerization of NBD to Q and the subsequent catalytic or thermally-induced conversion of Q to NBD are disclosed in U.S. Pat. No. 4,004,572 and by C. Philippopoulos et al., in *Ind. Eng. Chem. Prod. Res. Dev.* Vol. 22, 627–633 (1983), the disclosures of which are incorporated by reference herein.

The norbornadiene 1, which is employed in the present method is preferably selected from those which absorb substantial amounts of the photochemically effective solar spectrum range between about 300–700 nm or from those which can be photoisomerized to the corresponding quadricyclane with the aid of a sensitizer. Suitable inorganic and organic sensitizers for the conversion of norbornadiene (1, $R_1$=$R_2$=H) to quadricyclane (2, $R_1$=$R_2$=H) are disclosed by K. Maruyama et al., in *J. Org. Chem.*, 46, 5294 (1981), the disclosure of which is incorporated by reference herein.

Alternatively, the norbornadiene molecule can be substituted at one or more of its seven carbon atoms with a moiety which will allow the norbornadiene to absorb enough solar radiation to isomerize it to the corresponding quadricyclane. Useful norbornadienes of these types include those of the general formula 1 wherein R and R' are selected from the group consisting of (lower)alkoxycarbonyl, (lower)alkyl carbonyl, arylcarbamoyl (CONHAr), aryl, and mixtures thereof. Preferably R and R' are both arylcarbamoyl, R is arylcarbamoyl and R' is carboxy or R is lower(alkyl)carbonyl and R' is phenyl. The remaining positions of the norbornadiene molecule, $C_3$–$C_7$, can be H or can be substituted with substituents such as aryl or lower(alkyl). Preferred aryl substituents include phenyl, lower-(alkoxy)phenyl and lower(alkyl)phenyl, e.g. para-tolyl, while preferred alkyl groups include $C_1$–$C_4$-alkyl. Specific examples of the preparation of norbornadienes of this type and their conversion into the corresponding quadricyclanes are disclosed by K. Maruyama et al., in *J. Org. Chem.*, 46, 5294 (1981); K. Hirao et al., in *J. Chem. Soc., Chem. Commun.*, 300 (1984); K. Maruyama, *Chemistry Letters*, 839 (1981) and by H.-D. Scharf et al., in *Angew. Chem. Int. Ed. Engl.*, 18, 652 (1979), the disclosures of which are incorporated by reference herein.

As depicted in the FIGURE, energy release from quadricyclane 2 is initiated by the application of an anodic potential, which is applied to working electrode 12. Counterelectrode 17 is preferably maintained in a secondary reservoir 8, which contains solvent 20 and the electrolyte, but is otherwise maintained free of the reactants by means of a microporous barrier 7. Barrier 7 permits the passage of the charge-carrying electrolyte species necessary to maintain the electrical neutrality of the system, but blocks the passage of reactants from reservoir 11, and the reaction at electrode 17. The anodic current oxidizes carrier oxidant 6 to the corresponding cation radical 5, which then oxidizes quadricyclane 2 to the unstable cation radical 3, which spontaneously isomerizes to the corresponding norbornadiene cation radical with the liberation of heat ($\Delta$).

The oxidation potential of the neutral (uncharged) carrier oxidant compound must be sufficient to form the cation radical 3, but not so high that significant direct oxidation of quadricyclane 2 occurs at the electrode. Preferably oxidant 6 will be selected so that its oxidation potential $E^{o\prime}$ falls within about 0.3 V of the oxidation potential ($E_{\frac{1}{2}}^{ox}$) of the quadricyclane, and most preferably the $E^{o\prime}$ of the oxidant will be lower than the oxidation potential of the quadricyclane. For example an oxidant useful to initiate the conversion of quadricyclane ($E_{\frac{1}{2}}^{ox}=0.91$ V) would be selected to have an oxidation potential of about 0.5–0.7.

As depicted in the FIGURE, a preferred species of carrier oxidant 6 is a triarylamine ($Ar_3N\cdot$) wherein the aryl group is a phenyl group substituted so as to stabilize the cation radical 5 ($Ar_3N\cdot^+$), e.g. against self-condensation. Therefore, preferably Ar is a phenyl group substituted in the 4-, 2,4-, 3,4- or 3,5-positions with a lower-(alkyl) substituent. A (haloaryl)amine which is substantially stable under the photochemical conditions present can also be employed as the carrier oxidant. Useful triarylamines include tri-(para-substituted)amines such as tris(p-tolyl)amine and tris(p-bromophenyl)amine (Aldrich Chemical Co.). Methods for the preparation of triarylamines are disclosed in I. T. Harrison et al., *Compendium of Organic Synthetic Methods*, Wiley Interscience, N.Y. (1971) at pages 240–248, the disclosure of which is incorporated by reference herein.

Since the cation radical of the carrier oxidant need only be generated in catalytic amounts, the initial molar ratios of quadricyclane 2 to carrier (amine) 6 can be high, e.g. from about 20–500:1 or above.

Once formed, radical cation 4 is reduced, with the further generation of heat, to yield starting norbornadiene 1. Since radical cation 4 can itself abstract an electron from amine 6 (or from quadricyclane 2), the reaction is theoretically self-perpetuating. Although side reactions eventually could act to halt such reaction pathways, this aspect of the present method assists in minimizing the amount of current required to maintain the 2→3 oxidation, thus increasing the total energy efficiency of the present method. It is expected that the appropriate selection of quadricyclane, amine and solvent system will permit a net energy gain of up to about 100–1000:1 to be realized from the 2→1 isomerization.

The isomerization reaction can be stopped by the application of a cathodic current to electrode 12, which converts activator species 5, 5' back to the neutral species 6, 6'. Reapplication of the anodic current restarts the conversion of 2 to 3. The "switchable" nature imparted to the quadricyclane-norbornadiene isomerization reaction is an important feature of the present method, since it permits the controlled release of the thermal energy stored in a quadricyclane fuel, a necessary feature for the realization of a practical solar energy storage cell based on the quadricyclane to norbornadiene interconversion.

The reaction will be further described by reference to the following detailed examples.

EXAMPLE 1–CONVERSION OF QUADRICYCLANE TO NORBORNADIENE

Quadricyclane (0.01 mol of 2, R=R'=H, Aldrich Chemical Co.) and tris(p-tolyl)amine [$3.4 \times 10^{-4}$ mol, prepared according to the procedure of R. I. Walter, *J. Amer. Chem. Soc.*, 77, 5999 (1955)] were dissolved in 30 ml of methylene chloride containing 0.20M tetra-n-hexyl ammonium perchlorate (Pfaltz & Bauer, Stamford, Ct.) in a three compartment electrolysis cell, containing platinum wire working and reference electrodes and a saturated NaCl SCE reference electrode. Oxidation of the triarylamine carrier oxidant was performed at 0.3 V vs the reference electrode. This required a 10 V compliance potential. The current remained substantially constant at about 1 mA. The progress of the isomerization was followed both by coulometry and by GLC analysis. (See D. J. Fife et al., *J. Amer. Chem. Soc.*, 105, 7405 (1983) and K. Yasufuku et al., *Tetrahedron Letters*, 25, 4893 (1984), the disclosures of which are incorporated by reference herein. After 3.9 coulombs had passed, the quadricyclane had been quantitatively converted to norbornadiene (1, R=R'=H). On a molar scale, the amount of current required was equal to about 0.93 kcal/mol of quadricyclane converted to norbornadiene. In view of the thermal energy released, this constitutes better than a 25 to 1 energy gain, based on the compliance potential employed. Based on coulometry, the catalytic turnover was 247. This represents the average number of norbornadiene molecules produced from the corresponding quadricyclanes per triarylaminium ion generated by anodic oxidation.

The isomerization reaction was stopped instantly through the application of a cathodic potential and was restarted by reapplication of the anodic potential. Thus, the conversion of 2→1 could be turned on and off at will.

Since tris(p-tolyl)amine ($E^{o\prime}=0.66$ V) was oxidized more readily than 2, the oxidation of the amine and the single electron transfer from quadricyclane could be accomplished without electrode contamination. Replacement of tris(p-tolyl)amine with tris(p-bromophenyl)amine which has an $E^{o\prime}=1.02$ V resulted in some direct oxidation of quadricyclane to 3 (R=R'=H) at the electrode surface, resulting in slow deactivation of the electrode. Although the conversion continued after the current was interrupted, the reaction could also be stopped with a cathodic potential and restarted with an anodic potential.

Control experiments indicated that no change occurred in these systems after prolonged standing in the absence of current.

EXAMPLE 2—CONVERSION OF A SUBSTITUTED QUADRICYCLANE

In order to establish the generality of the present method, and to exemplify its use with a quadricyclane-norbornadiene pair where the photoreaction of 1→2 could be accomplished, substituted quadricyclane 2(R=Acetyl, R'=Phenyl) was prepared by the reaction of acetyl phenylacetylene with cyclopentadiene monomer to form substituted norbornadiene, followed by irradiation at 350 nm. Utilization of the present electrochemical "switching" process utilizing tris(p-tolyl)amine as the cation radical precursor quantitatively yielded the corresponding norbornadiene (1, R=Acetyl, R'=Phenyl) according to the procedures of Example 1.

The method of the present invention has been demonstrated to provide an electrically driven "on-off switch" for the release of thermal energy by the conversion of a quadricyclane to a norbornadiene. This method provides a much-needed component of any system intended to make use of this interconversion for solar energy storage and release.

The present invention has been described with reference to various specific and preferred embodiments and techniques. However it should be understood that many variations and modifications may be made while remaining within the spirit and scope of the invention.

What is claimed is:

1. A method for the electrochemical isomerization of a quadricyclane to a norbornadiene with the net release of thermal energy, said method comprising:
    (a) forming an electroconductive solution comprising said quadricyclane and a neutral carrier oxidant compound;
    (b) oxidizing said carrier oxidant compound to the corresponding cation radical of the oxidant compound by the application of an anodic potential to said solution;
    (c) oxidizing said quadricyclane to the corresponding quadricyclane cation radical by means of a single electron transfer from said quadricyclane to the cation radical of the oxidant compound, wherein the quadricyclane cation radical spontaneously isomerizes to the norbornadiene cation radical with the liberation of thermal energy; and
    (d) reducing the norbornadiene cation radical to the corresponding norbornadiene with the liberation of thermal energy.

2. The method of claim 1 wherein the norbornadiene cation radical is reduced by the extraction of an electron from the quadricyclane or from the neutral carrier oxidant compound.

3. The method of claim 1 further comprising stopping the conversion of the quadricyclane to the norbornadiene by the application of a cathodic potential to said solution.

4. The method of claim 3 further comprising restarting the conversion of the norbornadiene to the quadricyclane by the application of an the anodic potential of the said solution.

5. The method of claim 4 wherein the oxidation potential of said carrier oxidant compound is about 0.3 V less than that of the quadricyclane.

6. The method of claim 1 wherein the oxidation potential of said neutral carrier oxidant compound is within about 0.3 volts of the oxidation potential of the quadricyclane.

7. The method of claim 5 wherein the oxidation potential of said neutral carrier oxidant compound is no more than about 0.3 V lower than the oxidation potential of the quadricyclane.

8. The method of claim 1 wherein said neutral carrier oxidant compound is a triaryl amine.

9. The method of claim 8 wherein the triaryl amine comprises a [tri-(substituted-phenyl)]amine wherein the phenyl groups are individually alkylated at the 4-, 2,4-, 3,4- or 3,5-ring positions.

10. The method of claim 9 wherein the triarylamine comprises a [tri-($C_1$–$C_4$-alkylated)phenyl]amine.

11. The method of claim 1 wherein said norbornadiene is converted into said quadricyclane by the absorption of light in the wavelength region of about 300–700 nm or by means of a photosensitized reaction.

12. The method of claim 1 wherein said norbornadiene is converted to said quadricyclane under solar irradiation.

13. The method of claim 11 wherein said norbornadiene is a 2,3-disubstituted norbornadiene wherein the substituents are selected from the group consisting of (lower)alkoxycarbonyl, (lower)alkylcarbonyl, arylcarbamoyl, aryl and mixtures thereof.

14. The method of claim 13 wherein the norbornadiene comprises 3-phenylcarbamoyl-2,5-norbornadiene-2-carboxylic acid, 2,3-bis(methoxy carbonyl)norbornadiene or 2-acetyl-3-phenyl-2,5-norbornadiene.

* * * * *

UNITED STATES PATENT AND TRADEMARK OFFICE
CERTIFICATE OF CORRECTION

PATENT NO. : 4,582,578

DATED : April 15, 1986

INVENTOR(S) : Paul G. Gassman
            James W. Hershberger

It is certified that error appears in the above-identified patent and that said Letters Patent is hereby corrected as shown below:

At column 3, line 4, for "form" read --from--.

At column 4, line 27, for "(hy)" read --(hµ)--.

Signed and Sealed this

Nineteenth Day of August 1986

[SEAL]

Attest:

DONALD J. QUIGG

Attesting Officer

Commissioner of Patents and Trademarks